United States Patent [19]

Tiwari et al.

[11] Patent Number: 4,601,810
[45] Date of Patent: Jul. 22, 1986

[54] ELECTROCHEMICAL PROBE FOR MEASURING MAGNESIUM CONCENTRATION IN MOLTEN ALUMINUM

[75] Inventors: Basant L. Tiwari, Sterling Heights; Blake J. Howie, Romeo, both of Mich.

[73] Assignee: General Motors Corporation, Detroit, Mich.

[21] Appl. No.: 783,361

[22] Filed: Oct. 3, 1985

[51] Int. Cl.$^4$ ............................................. G01N 27/58
[52] U.S. Cl. .................................... 204/413; 204/1 T; 204/400
[58] Field of Search ............... 204/400, 413, 1 T, 422, 204/423

[56] References Cited

U.S. PATENT DOCUMENTS

| | | | |
|---|---|---|---|
| 3,565,769 | 2/1971 | Holden et al. | 204/1 T |
| 3,794,569 | 2/1974 | Kawai et al. | 204/195 |
| 3,816,269 | 6/1974 | Wilder | 204/195 |
| 4,166,009 | 8/1979 | Fray | 204/195 |

OTHER PUBLICATIONS

Lukashenko and Pogodoyev, "The Thermodynamic Functions of Liquid Mg—Al Alloys", Russian Metallurgy (1971).

G. K. Belton and Y. K. Rao, "A Galvanic Cell Study of Activities in Mg—Al Alloys", Transactions of the Metallurgical Society of AIME, 245, 2189–2193, (1969).

Primary Examiner—G. L. Kaplan
Attorney, Agent, or Firm—Lawrence B. Plant

[57] ABSTRACT

An electrochemical concentration cell adapted for immersion in a melt of aluminum-magnesium alloy for determining the concentration of the Mg on an ongoing basis (e.g., during demagging). The cell includes a first probe comprising a housing having a cavity therein containing a Mg-ion-rich molten salt electrolyte. An opening in the housing exposes the electrolyte to the melt via a porous ceramic frit wetted by the electrolyte. A hollow capsule containing a Mg-rich reference material is immersed in the electrolyte and the reference material electrically coupled to the melt via second probe immersed therein. Containment of the reference material within the capsule beneath the melt prevents attack of the housing by the reference material and evaporative loss thereof.

3 Claims, 2 Drawing Figures

ELECTROCHEMICAL PROBE FOR MEASURING MAGNESIUM CONCENTRATION IN MOLTEN ALUMINUM

This invention relates to devices for measuring the concentration of magnesium in molten aluminum and more particularly to an electrochemical device for substantially continually monitoring the magnesium concentration in molten aluminum alloys.

Secondary aluminum (e.g., aluminum scrap) often contains undesirable quantities of magnesium which must be removed before the aluminum can be reused for many applications. Magnesium removal is typically accomplished by the so-called "chlorine demagging" process wherein gaseous chlorine is injected into the aluminum melt to consume the magnesium and to reduce its concentration down to about 0.1 weight percent or less. In such chloridization processes the last stage of chlorination is very inefficient and a large amount of aluminum Tri-chloride pollutant can be generated if the magnesium concentration is not closely monitored.

Electrochemical measurement (i.e., concentration cells) of the concentration of one metal in another has been proposed (e.g., see U.S. Pat. Nos. 3,816,279, 3,794,569, or 4,166,009). Moreover, Lukashenko and Pogodoyev, "The Thermodynamic Functions of Liquid Mg—Al Alloys", *Russian Metallurgy* (1971), and G. K. Belton and Y. K. Rao, "A Galvanic Cell Study of Activities in Mg—Al Liquid Alloys", *Transactions of the Metallurgical Society of AIME*, 245, 2189-2193, (1969) have used electrochemical concentration cells to determine the activities in Mg—Al alloys. To our knowledge, however, such techniques have not been used effectively to continuously measure low concentrations of magnesium in molten aluminum in an ongoing production situation. Rather, at the present time, magnesium content in the melt is usually determined by either chemical analysis or mass spectrometry. Both of these methods, however, are time consuming and therefore not commercially practical to monitor magnesium concentration on an ongoing basis in the course of processing. It is not known why analytical devices like those of Lukashenko et al or Belton et al have not been used for monitoring aluminum demagging processes. However, we believe it is likely due to the very short-lived character of their cell designs which (1) expose the cell housing to attack by concentrated magnesium (i.e., from the reference material) and (2) provide no means to prevent evaporation of magnesium reference material from the surface of the electrolyte on which it floats.

It is therefore an object of the present invention to provide a long-lived, reliable electrochemical device for monitoring low levels of magnesium in aluminum melts on an ongoing basis and during the course of processing (e.g., demagging) the melt. This and other objects and advantages of the present invention will become more readily apparent from the description thereof which follows.

BRIEF DESCRIPTION OF THE INVENTION

The present invention comprehends a device for electrochemically determining the concentration of magnesium in an aluminum alloy containing small quantities of magnesium (e.g., melts containing secondary aluminum). The device operates on the well known principle of a concentration cell and measures the potential difference between the magnesium-containing alloy and a reference material having a known magnesium content (e.g., pure magnesium or magnesium silicide) and separated one from the other via a magnesium-ion-containing fused salt electrolyte (e.g., $MgCl_2$). More specifically, the device includes two probes for immersion into the melt. The first probe is nothing more than a conductor which is substantially inert to (e.g., unalloyable with) aluminum and serves to contact the melt for closing the electrical circuit between it and the reference material. The second probe comprises an impervious, preferably tubular, housing which is substantially inert to and unalloyable with the aluminum melt whose magnesium content is to be measured. The housing has a cavity therein which contains the essential elements of the concentration cell. In the case of a tubular housing, the cavity will comprise the central bore of the tube and the cell elements will be located at the end of the tube which is to be immersed into the melt. More specifically, the end of the tube which is to be immersed in the melt is sealed off with a porous ceramic frit which when wetted with molten salt electrolyte holds the electrolyte in place by surface tension at the end of the tube and prevents it from escaping the tube while at the same time providing an ionic path into the cavity from the melt. The frit-containing end of the tube is filled with a pool of magnesium-containing salt electrolyte (e.g., $MgCl_2$—$CaCl_2$ eutectic). The reference material is housed in an open-ended capsule (preferably electrically conductive) which is immersed in the electrolyte such that the reference material contacts the electrolyte (i.e., at the open end of the capsule) but cannot escape the capsule. In this regard it has been found to be important to trap the magnesium reference material beneath the electrolyte to prevent it from either attacking the housing or evaporating and thereby prolonging the life of the probe. The reference material will preferably comprise pure magnesium, though other magnesium-rich materials may be used so long as the other ingredients mixed with the magnesium will not affect the quality and reliability of the cell potential produced as an indicator of the magnesium concentration in the melt. The reference material is electrically connected to the conductor used to contact the melt via an electrically conductive lead which, in the preferred embodiment, extends the length of the bore in the tube and exits the other end of the tube. The electrical lead passes through an inner plug which substantially fills the bore in the tube in a region slightly above the level of the molten salt electrolyte in the tube. The plug serves to retain the electrolyte at the frit end of the tube as well as substantially prevent any significant evaporation of the electrolyte. A volt meter between the two probes measures the EMF therebetween. Calibration graphs are prepared with the specific reference material chosen by measuring the EMF generated using that material with the probe immersed in several different aluminum alloy melts of known magnesium concentration. Thereafter when the probes are immersed in melts of unknown magnesium concentration the EMF between the two probes is measured and compared to the calibration graphs to determine the magnesium concentration thereof.

DETAILED DESCRIPTION OF A SPECIFIC EMBODIMENT

Figure 1:
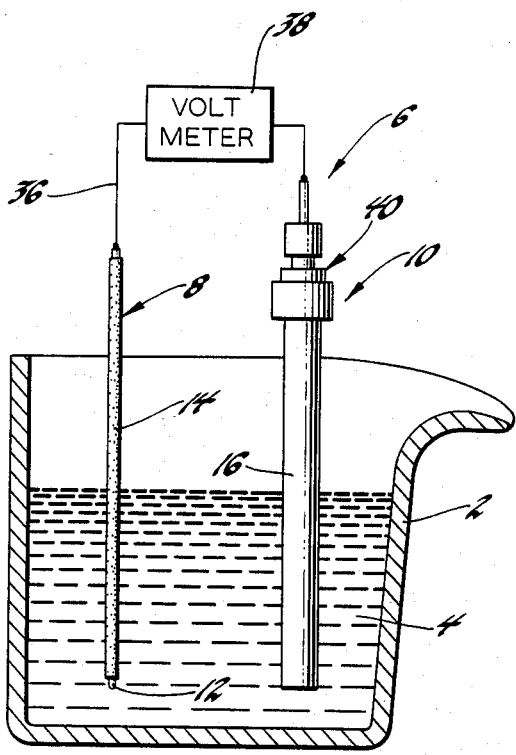
Figure 2:
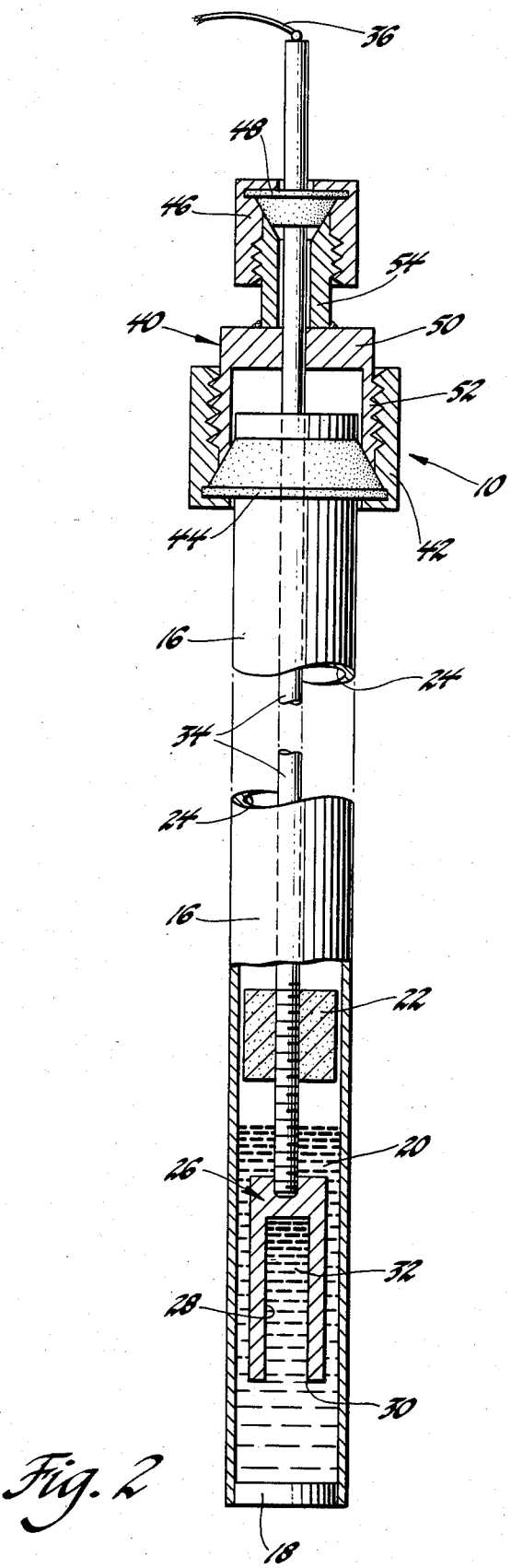

The invention may better be understood by reference to the following detailed description of a preferred embodiment thereof which is given hereafter in conjunction with the several drawings in which:

FIG. 1 is a side, partially sectioned, view of an aluminum filled ladle with the device of the present invention (oversized for illustration) in position for use; and FIG. 2 is a partially broken away, sectioned view of the cell-containing probe of the present invention.

FIG. 1 depicts a ladle 2 filled with an aluminum alloy melt 4 contaminated with magnesium. A magnesium concentration measuring device 6 is immersed in the melt 4 and comprises a first probe 8 for establishing electrical contact with the melt 4 and a second probe 10 which is the subject of the present invention. The first probe 8 is simply an electrical conductor for conducting current out of the melt 4 and preferably comprises a molybdenum rod 12 having an alumina coating or sheath 14 thereon. Other electrical conductors inert to the aluminum melt, such as carbon or titanium boride, might also be used instead of the molybdenum.

FIG. 2 depicts the electrochemical probe which is the heart of the present invention and shows a tubular housing 16 comprised of a material which is inert to molten aluminum. The tube 16 will preferably comprise alumina but may alternatively comprise boron nitride or even a metal, such as steel, coated with alumina to protect it from the aluminum. A porous alumina or boron nitride frit 18 is fitted into the end of the tube 16 which is to be immersed into the melt 4. The frit is sufficiently porous to permit water to run therethrough but when wetted by molten salt electrolyte will retain the molten salt therein by capillary action. The frit-bearing end of the tube is filled with a molten salt electrolyte 20, which electrolyte will include at least one magnesium-containing salt and preferably comprise a eutectic mixture of magnesium chloride and calcium chloride. An impervious plug 22 comprising alumina or boron nitride substantially fills the bore 24 in the tube 16 and substantially contains the molten salt electrolyte 20 at the end of the probe 10, i.e., between the plug 22 and the frit 18. A hollow conductive capsule 26 is immersed in the electrolyte 20 and defines a pocket 28 which opens to the electrolyte 20 via an opening 30 in the capsule 26. A magnesium-containing reference material 32 (i.e., preferably pure magnesium) is contained (i.e., trapped) within the cavity 28 and is thereby prevented from rising to the surface of the electrolyte 20 or directly attacking the inside of the alumina tube 16. In the embodiment shown and with the probe oriented in the vertical direction, containment of the reference material within the cavity 28 is provided by gravity alone as the magnesium 32 is lighter than the electrolyte 20 and is therefore trapped within the cavity 28 by floatation. Alternatively, the cavity 28 may be provided with an open pore molybdenum mesh or screen of high porosity which holds the molten magnesium by capillary action and hence prevents escape thereof in the event the probe is turned or otherwise misoriented while the electrolyte and magnesium are molten. A molybdenum shaft 34 extends from the capsule 26 through the plug 22 and out the top of the tubular housing 16 and is connected to the probe 8 via the wires 36 and volt meter 38.

The molybdenum shaft 34 is secured to the end of the tube 16 which projects from the melt 4 via an appropriate compression fitting 40. More specifically, the female or cap portion 42 of the compression fitting 40 includes a Teflon ferrule 44 which fits snugly about the tubular housing 16 while the female cap portion 46 of the compression fitting 40 includes a Teflon ferrule 48 snugly engaging the molybdenum shaft 34. The central or body portion 50 of the compression fitting 40 includes a first male portion 52 for engaging the female portion 42 and a second male portion 54 for engaging the female portion 46. Tightening of the female portions 42 and 46 onto the male portions 52 and 54, by means of the threads provided, causes the ferrules 44 and 48 to compressively engage the tube 16 and shaft 34 respectively as is well known for such compression fittings.

According to one specific example of a probe in accordance with the present invention, a probe was made comprising a dense alumina tube having an outside diameter of 0.56 cm, an inside diameter of 0.47 cm and a length of 55 cm. The end of the tube which was to be immersed in the melt was plugged with a porous alumina frit by filling it with an alumina paste (i.e., TAYCOR Cement Brand 320) made by the Chas. Taylor & Sons Company and heating it slowly to 1000° C. in air to remove the volatiles and form the porous frit. The frit was sufficiently porous that water introduced into the tube would flow through the frit under gravity alone, but would nonetheless contain molten electrolyte by capillary action when the tip of the probe was immersed into the molten aluminum. 1.1 grams of $CaCl_2$—$MgCl_2$ eutectic was placed inside the tube above the frit. A molybdenum capsule was immersed in the electrolyte and comprised a 0.50 cm cylinder having a 0.4 cm bore drilled in the end thereof to receive the magnesium reference material. This device demonstrated no erratic fluctuations in cell potential (as had been observed in earlier probe designs tested) over a test period of seven days. At the end of the tests, autopsy of the probe showed no sign of reaction between magnesium and the alumina housing and the capsule remained full of magnesium.

While the invention has been disclosed primarily in terms of specific embodiments thereof it is not intended to be limited thereto but rather only to the extent set forth hereafter in the claims which follow.

The embodiments of the invention in which an exclusive property or privilege is claimed are defined as follows:

1. An electrochemical cell adapted for immersion in a melt of Al alloy containing small quantities of Mg for determining the concentration of said Mg in said melt comprising: an impervious housing which is substantially inert to molten Al; a cavity in said housing; an opening in said housing communicating said cavity with said melt when immersed therein; a porous ceramic electrolyte-wettable frit sealed in said opening; a pool of molten salt magnesium-ion-containing electrolyte filling the pores of said frit and a portion of said cavity; capsule means immersed in said electrolyte; a pocket within said capsule; said capsule having an aperture therein submerged beneath said electrolyte and communicating said pocket with said electrolyte; a Mg-rich reference electrode material contained within said pocket out of contact with said housing and in direct communication with said electrolyte via said aperture, said material consisting essentially of magnesium; electrical lead means engaging said reference material for conducting current from said material externally of said housing; conductor means connected to said lead means for immersion in said melt; and means for measuring the electrochemical potential between said conductor means and said reference material for comparison to a predetermined calibration graph prepared with said reference material from known concentrations of Mg in Al alloys.

2. An electrochemical cell adapted for immersion in a melt of Al alloy containing small quantities of Mg for determining the concentration of said Mg in said melt comprising: an impervious housing which is substantially inert to molten Al; a cavity in said housing; an opening in said housing communicating said cavity with said melt when immersed therein; a porous electrolyte-wettable ceramic frit sealed in said opening; a pool of molten $MgCl_2$-containing electrolyte filling the pores of said frit and a portion of said cavity; an electrically conductive capsule immersed in said electrolyte; a pocket within said capsule; said capsule having an aperture therein submerged beneath said electrolyte and communicating said pocket with said electrolyte; a Mg-rich reference electrode material contained within said pocket out of contact with said housing and in direct communication with said electrolyte via said aperture, said material consisting essentially of magnesium; electrical lead means engaging said capsule for conducting current from said capsule externally of said housing; conductor means connected to said lead means for immersion in said melt; and means for measuring the electrochemical potential between said conductor means and said reference material for comparison to a predetermined calibration graph prepared with said reference material from known concentrations of Mg in Al alloys.

3. An electrochemical cell adapted for immersion in a melt of Al alloy containing small quantities of Mg for determining the concentration of said Mg in said melt comprising: an impervious tube which is substantially inert to molten Al; a central bore extending the length of said tube; a porous ceramic frit sealed in one end of said bore for immersion into said melt; a pool of molten $MgCl_2$—$CaCl_2$ electrolyte filling the pores of said frit and a portion of said bore; an electrically conductive capsule immersed in said electrolyte; a pocket within said capsule; said capsule having an aperture therein submerged beneath said electrolyte and communicating said pocket with said electrolyte; a Mg-rich reference electrode material contained within said pocket out of contact with said tube and in direct communication with said electrolyte via said aperture, said material consisting essentially of magnesium; electrical lead means engaging said capsule for conducting current from said capsule externally of said tube; plug means substantially filling the bore between said lead means and said tube to substantially contain said electrolyte within said tube between said plug means and said frit; conductor means connected to said lead means for immersion in said melt; and means for measuring the electrochemical potential between said conductor means and said reference material for comparison to a predetermined calibration graph prepared with said reference material from known concentrations of Mg in Al alloys.

* * * * *